ant Patent [19]

Trubac

[11] Patent Number: 4,814,517
[45] Date of Patent: Mar. 21, 1989

[54] OXYGENATE REMOVAL IN MTBE PRODUCTION

[75] Inventor: Robert E. Trubac, Ridgewood, N.J.

[73] Assignee: UOP, DesPlains, Ill.

[21] Appl. No.: 204,301

[22] Filed: Jun. 9, 1988

[51] Int. Cl.$^4$ ............................................. C07C 41/06
[52] U.S. Cl. .................................... 568/697; 568/699
[58] Field of Search ................................ 568/697, 699

[56] References Cited

U.S. PATENT DOCUMENTS 4,404,118 9/1983 Herskovits ...................... 252/411 R
4,447,653 5/1984 Vora .................................... 568/697
4,504,688 3/1985 Herwig et al. ...................... 568/697

Primary Examiner—Howard T. Mars
Attorney, Agent, or Firm—Richard G. Miller

[57] ABSTRACT

Low concentrations of methanol and dimethyl ether in distillation column $C_4$–$C_5$ raffinate produced in the formation of methyl tert.-alkyl ethers by the reaction of methanol with isoalkylenes are effectively removed from the residual $C_4$–$C_5$ hydrocarbons by adsorption on a dual or compound adsorption bed containing silica gel as the methanol adsorbent and zeolite 13X as the dimethyl ether adsorbent.

4 Claims, 1 Drawing Sheet

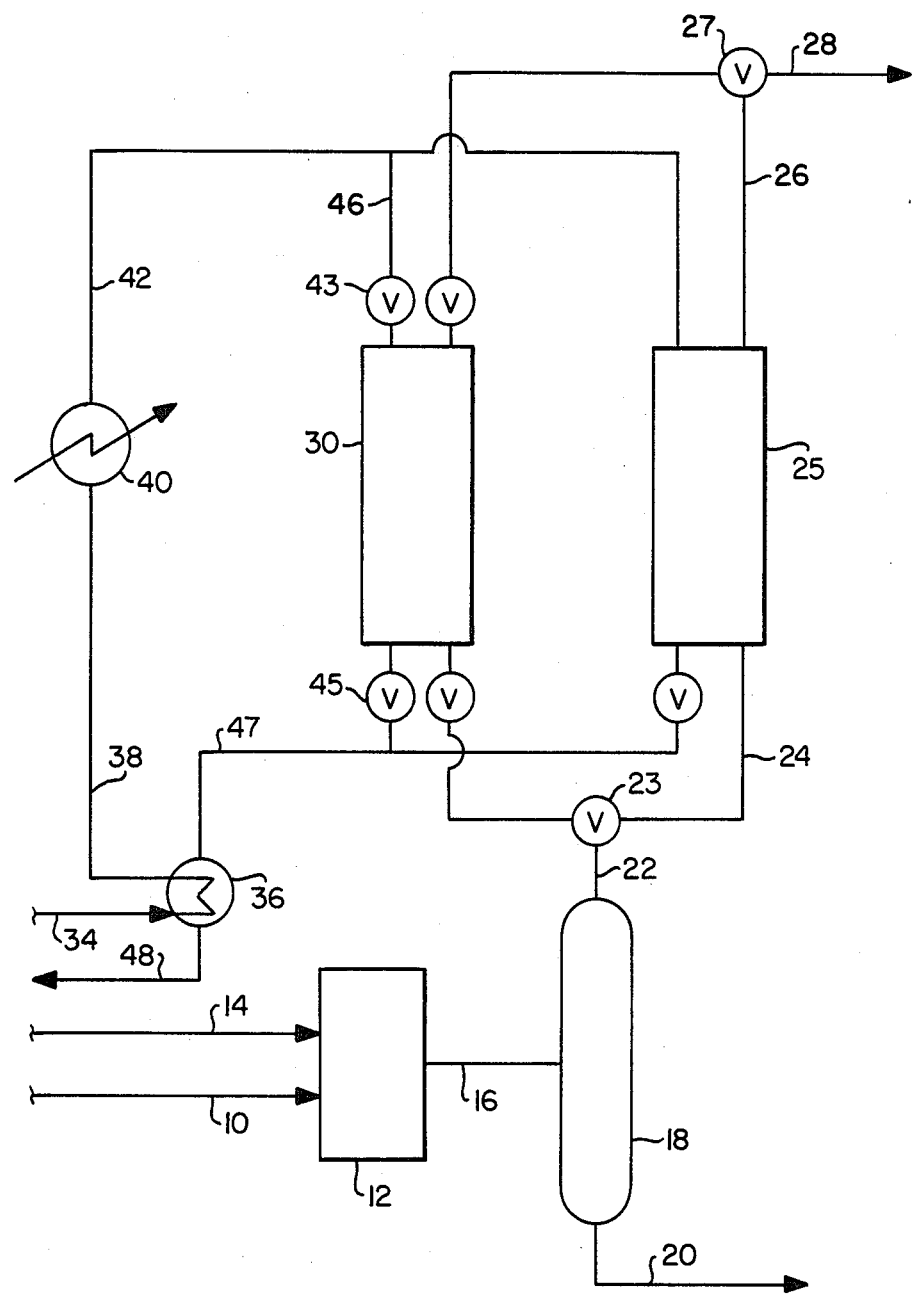

OXYGENATE REMOVAL IN MTBE PRODUCTION

The present invention relates to a process for the production of ethers by the reaction of an alcohol with an isoolefin. The invention more particularly relates to the preparation of methyl tert.-butyl ether and methyl tert.-amyl ether by the reaction of methanol with isobutylene and isoamylene respectively. The invention specifically relates to the selective removal of methanol and at least one other oxygenated hydrocarbon from a stream comprising unreacted $C_4$ or $C_5$ hydrocarbons which commonly is the overhead from a distillation column used to recover the bulk of the ether product from the reactor.

BACKGROUND OF THE INVENTION

The production of ethers by the reaction of an isoolefin and an alcohol is a well-known commercial operation. A number of detailed descriptions of such processes, particularly as they relate to the production of methyl tert.-butyl ether (MTBE) and methyl tert.-amyl ether (MTAE) are useful as high octane blending agents for gasoline motor fuels by virtue of their high Research Octane Number (RON) of about 120. Perhaps the most commonly employed reaction in the preparation of MTBE and MTAE is that between methanol and isobutylene or isoamylene, respectively. A wide variety of catalyst materials have been found to promote this reaction including ion-exchange resins such as divinylbenzene cross-linked polystyrene ion exchange resins in which the active sites are sulfuric acid groups; and inorganic heterogeneous catalysts such as boric acid, bismuth molybdate, and metal salts of phosphomolybdic acids wherein the metal is lead, antimony, tin, iron, cerium, nickel, cobalt or thorium. Also boron phosphate, blue tungsten oxide and crystalline aluminosilicates of the zeolitic molecular sieve type have also been proposed as heterogeneous catalysts for the reaction of methanol and isobutylene.

The preference for the isoalkylene-methanol reaction is in part, at least, due to the relative abundance of the starting materials. Both isobutylene and isoamylene are readily available in a petroleum refinery from both fluid catalytic crackers and as a by-product of ethylene production. Methanol is, of course, a staple commercial chemical of long standing. Moreover, isobutylene, because of its volatility, cannot be added to the gasoline pool without alkylation. Methanol cannot be added to gasoline in significant quantities because of immiscibility problems and because of its corrosiveness toward existing internal combustion engines. The combining of these two compounds thus appears to be an advantageous way to extend the gasoline pool. The modification of a gasoline by the conversion of 2-methyl-1-butene and 2-methyl-2-butene to methyl tert.-amyl ether is proposed in U.S. Pat. No. 3,482,952.

In addition to being useful in the preparation of high octane ethers for gasoline up-grading, the etherification process is also useful as a separation process. The reaction of methanol with mixed $C_4$ and $C_5$ olefins is selective for the isobutylene and isoamylene isomers. Therefore, a mixed butylene and/or amylene stream common to refineries can use the aforesaid etherification process to separate this mixture and to produce a stream of essentially pure normal butenes and/or amylenes and essentially pure MTBE and/or MTAE. The ethers can subsequently be cracked to produce essentially pure isoalkylenes.

A wide variety of reaction conditions have heretofore been proposed for carrying out the reaction of isobutylene or isoamylene with methanol, depending in part upon the type of catalyst employed in each case. Thus, both vapor phase and liquid phase processes are known in which reaction temperatures are from about 50° C. to about 400° C., pressures vary from atmospheric to 1,500 psig, and the mole ratios of methanol to isoalkylene range from 0.1:1.0 to about 10:1. Both batch type and continuous process schemes are said to be suitably employed.

It is commonly the case that the source of isobutylene is a mixed $C_4$ hydrocarbon stream from a refinery operation, and the reaction with methanol is carried out in the liquid phase at a temperature not exceeding 100° C. The quantity of the MTBE produced depends upon the isobutylene content of the $C_4$ hydrocarbon stream used. When a $C_4$ hydrocarbon stream cut from steam cracking is used, providing a feedstock with approximately 50% isobutylene after butadiene extraction, the reactor effluent can contain almost 60% MTBE and can sometimes be used as a gasoline component without further treating. It is generally more desirable, however, to separate the unreacted $C_4$'s from the reactor effluent by distilling off the unconverted $C_4$'s. When this is done, MTBE of about 98% purity can be produced at an isobutylene conversion of about 95%. A further increase in the conversion, based on isobutylene, can be achieved only by using a higher methanol/isobutylene ratio in the reactor feedstock. Because greater than stoichiometric amounts of methanol are used in the high conversion MTBE processes (also to allow for fluctuating isobutylene concentrations), additional steps have to be included in such processes to recover the excess methanol from reactor effluent. The recovered methanol is then recycled to the reactor feed stream.

To avoid the need for recycle of the unreacted methanol and for other reasons, such as to optimize reaction section costs, it is sometimes desirable to regulate the methanol feed to the MTBE reactor to less than stoichiometric amounts with respect to isobutylene. While the presence of methanol in the reactor effluent is not thereby entirely eliminated, the methanol content in the effluent can be significantly lowered, typically to 1000 to 6000 ppm (weight). Since the reactor effluent also contains other oxygenates which are advantageously not recycled to the reactor, recovery of the relatively small amount of methanol in a pure form for recycle is not, in general, economically feasible. On the other hand, the reactor effluent commonly contains $C_4$ and/or $C_5$ hydrocarbons other than the isoalkylene species in appreciable amounts due to the fact that the isoalkylene feed to the reactor is a mixture thereof with other $C_4$ or $C_5$ hydrocarbons. Such feeds are commonly derived from a fluidized catalytic cracking process wherein the isoalkylene usually constitutes only 12 to 16% of the total $C_4$ and/or $C_5$'s. These hydrocarbons are valuable substrates for catalytic alkylation or isomerization processes and are usually further processed in that manner, but only after purification to remove the oxygenated hydrocarbon impurities such as dimethyl ether and methanol which are harmful to the catalyst compositions employed.

For the purpose of adsorbing all of the oxygenates from such $C_4$–$C_5$ hydrocarbon by-product streams from MTBE and MTAE processes, the entire general class of solid adsorbents has been proposed. These include sorbents which function by a chemisorption mechanism as well as physical adsorption such as silica gel, activated aluminas, activated carbon, crystalline zeolite molecular sieves, clays and ion exchange resins. The zeolite molecular sieves have generally been the preferred adsorbents, with zeolite 5A, zeolite 13X and zeolite D (a synthetic zeolite topologically related to the mineral chabazite) being specified in several publications, namely U.S. Pat. No. 4,447,653 (Vora); U.S. Pat. No. 4,404,118 (Herskovits) and U.S. Pat. No. 4,465,870 (Herskovits). Activated alumina is the adsorbent required in the process of U.S. Pat. No. 4,371,718 (Hutson, Jr.) and an absorber resin is found by Herwig et al (U.S. Pat. No. 4,504,688) to be superior for methanol absorption.

STATEMENT OF THE INVENTION

It has now been discovered that the hydrocarbon raffinate from a distillation column used to recover MTBE or MTAE from the reactor effluent, said raffinate containing at least 50 ppm (w) methanol and at least 5 ppm (w), preferably 5 to 3,000 ppm (w) dimethyl ether, can be treated to remove the dimethyl ether and the methanol by passing the raffinate stream in the liquid phase through a first adsorbent zone containing silica gel as the adsorbent, whereby the methanol is selectively adsorbed, and thereafter passing in the liquid phase the effluent from said first adsorbent zone through a second adsorbent zone containing sodium zeolite X as the adsorbent.

It is surprisingly found that silica gel is both highly selective in the adsorption of methanol vis-a-vis dimethyl ether and has a capacity for adsorbed methanol under the usual process conditions of as much as two times that of zeolite 13X Further, zeolite 13X has a very strong adsorption affinity for dimethyl either and in the relative absence of methanol is capable of reducing the dimethyl ether content of the $C_4$-$C_5$ hydrocarbon raffinate to the low levels desired. It has been discovered that combining a silica gel bed with a zeolite 13X bed, a compound adsorption bed is created which is much superior to beds using either type of adsorbend alone. Also the superior mass transfer characteristics of zeolite 13X with respect to silica gel greatly contribute to the superiority of the compound bed in the present process.

Accordingly, the present invention resides in the cyclic process for preparing methyl tert.-alkyl ether which comprises the steps of (a) contacting and reacting in the liquid phase a reaction mixture formed by combining a stream consisting essentially of hydrocarbons having from 4 to 5 carbon atoms and containing at least some proportion of an isoalkylene having from 4 to 5 carbon atoms with less than a stoichiometric excess of methanol, with respect to the isoalkylene, to form a reaction product comprising methyl tert.-alkyl ether, at least 50 ppm (w) unreacted methanol, unreacted $C_4$-$C_5$ hydrocarbons and at least 5 ppm (w) dimethyl ether;

(b) isolating at least 99 percent (v) of the methyl tert.-alkyl ether from the reaction product;

(c) recovering the unreacted methanol and dimethyl ether from the residual portion of the reaction product by passing said residual portion in the liquid phase and at a temperature of less than 60° C. through a first adsorption zone containing silica gel as the adsorbent whereby the methanol is selectively adsorbed thereon and thereafter passing the effluent from said first adsorption zone through a second adsorption zone containing zeolite 13X as the adsorbent whereby dimethyl ether is selectively adsorbed and non-adsorbed $C_4$-$C_5$ hydrocarbons are removed therefrom as the effluent and recovered;

(d) regenerating the two adsorption zones by passing therethrough a non-sorbable purge fluid stream in such a manner that the purge fluid stream passes first through the said second adsorption zone and thereafter the effluent therefrom passes through the first adsorption zone whereby the second adsorption zone is not contacted with methanol desorbed from the first adsorption zone; and (e) recovering additional methanol and dimethyl ether respectively in the said first and second adsorption zones by passing an additional residual portion of the reaction product as defined in step (c) through the regenerated adsorption zones.

The two adsorption zones can be formed whether by connecting two separate fixed adsorption beds in series, or by preparing a single compound bed in which the silica gel is positioned at one end of the bed and the 13X zeolite at the other. The relative quantities of each adsorbent will depend upon the relative concentrations of methanol and dimethyl ether in the $C_4$-$C_5$ hydrocarbon feedstock being treated. Absolute quantities of each adsorbent are similarly dependent upon the absolute concentrations of each adsorbate in the feedstock. During regeneration, the flow of purge fluid is countercurrent to the flow of the feedstock through the bed during adsorption, the latter entering the end of the bed containing the silica gel.

BRIEF DESCRIPTION OF THE DRAWINGS

The drawings are a schematic flow diagram of a process system suitable for the preparation of MTBE.

The following description of the present process with respect to the production of MTBE is made with reference to the flow diagram of the drawings. In the interest of simplifying the description of the invention, the process system in the drawing does not contain the several conduits, valves and the like which in actual practice would be provided in accordance with routine skill in the art to enable the process to be carried out continuously.

Methanol in the liquid phase enters the reaction system through line 10 and enters the reactor 12 along with a $C_4$ hydrocarbon liquid stream comprising isobutylene entering through line 14. Advantageously, all fluid streams introduced into the system have previously been dried to a water dew point of 0° C. to 10° C. at the operating pressure of the reactor. Reactor 12 is operated at a temperature which in large measure is dependent upon the particular catalyst employed but is generally in the range of about 40° C. to 90° C. and using an internal system pressure sufficient to maintain the reaction mixture in the liquid phase. In the present embodiment, the catalyst is of the ion-exchange resin type and the temperature of the reactor is about 60° C. The isobutylene-containing $C_4$ hydrocarbons including butene-1, cis and trans butene-2, butadiene, isobutane and n-butane along with the isobutylene. Preferably the isobutylene is present in an amount of at least 10 mol-%. The molar ratio of methanol to isobutylene is less than 1.0. The effluent from the reactor comprises product MTBE, unreacted methanol, unreacted $C_4$'s and dimethyl ether in addition to other reaction by-products. This effluent is passed through line 16 to distillation unit 18. While in this illustration the reactor and distillation tower are represented as two separate apparatuses, relatively recent advances have made possible the combination of the function of the reactor and the distillation tower into a single piece of apparatus. For purposes of the present invention, either operational mode is suitably employed. As a result of the distillation process, MTBE product is recovered from the bottom and is removed from the system through line 20. The overhead effluent from the distillation tower comprises from about 4000 ppm (w) unreacted methanol, unreacted $C_4$ hydrocarbons, 200 to 400 ppm (w) dimethyl ether as well as trace amounts of other volatile by-products. This effluent passes through line 22, valve 23 and line 24 to compound adsorbent bed 25 containing in the ingress (bottom) end a commercially available silica gel adsorbent and in the egress (top) end zeolite 13X (sodium zeolite X). The temperature within the adsorption bed is preferably at an initial temperature of from 30° C. to 120° C. The actual bed temperature will depend upon the temperature of the purge fluid used to desorb the bed during the previous bed regeneration. The effluent from the distillation unit 18 is at a temperature of from about 30° C. to 80° C. and enters bed 25 without being cooled. The pressure in bed 25 is maintained such as to cause the dimethyl ether and methanol-containing $C_4$ fluid stream being treated therein to be in the liquid phase. The effluent from bed 25 contains from about 0 to 10 ppm(w) methanol and about 0 to 10 ppm(w) dimethyl ether, with the balance being principally a mixture of olefinic and saturated n-$C_4$ hydrocarbons. This effluent is passed through line 26, valve 27 and line 28 and can be removed from the process system without further treatment and utilized as feed for an alkylation unit. While the adsorption step is being carried out in bed 25, bed 30, which is essentially identical with bed 25 insofar as configuration and loading with silica gel and zeolite 13X is concerned, is being regenerated after previous service in methanol and dimethyl ether removal from the raffinate from distillation unit 18. The regeneration of bed 30 is accomplished in the conventional manner by purging in a direction countercurrent to the direction of flow through the bed during the adsorption step therein, using n-butane which enters the system through line 34 and passes through heat-exchanger 36, line 38 and heater 40 wherein its temperature is raised to the range of at least 50° C. (122° F.), preferably at least about 80° C. to about 115° C. The pressure conditions are controlled to maintain the n-butane stream through bed 30 substantially in the liquid phase. From heater 40 the n-butane stream is passed through lines 42 and 46 and valve 43 into adsorbent bed 30. The effluent desorbed methanol, dimethyl ether and n-butane purge stream from bed 30 are passed through valve 45 and line 47 to heat exchanger 36 and is removed from the system through line 48. The purge-regeneration of bed 30 is continued until desired level of residual methanol, and dimethyl ether loading is achieved. If the dimethyl ether is recycled to the reactor, under properly controlled, conditions, there results an advantageous decrease in the amount of dimethyl ether formed in the reactor. That aspect, however, is not an essential feature of the present invention. At this point adsorption bed 25 is at the end of the adsorption stage in its operation and is ready to be regenerated as described above with respect to bed 30.

As will readily be apparent to those skilled in the art, it is not necessary to regenerate the adsorption beds with the n-butane. Any non-sorbable purge fluid, either in the vapor phase or the liquid phase can be utilized. A convenient source of a preferred regeneration medium is a portion of the purified $C_4$–$C_5$ hydrocarbon product after passage through the adsorption-purification system.

As a demonstration of the importance of introducing the methanol and dimethyl ether-containing feedstock into the compound bed in a direction such that the adsorbed first contacted consists essentially of silica gel rather than zeolite 13X, two compounds beds were prepared. Bed A contained equal quantities of zeolite 13X and silica gel with the bulk of the zeolite adsorbent being located at the ingress end of the bed and the bulk of the silica gel being located at the egress end. Bed B contained only 33 percent of the total adsorbent as zeolite 13X, and the silica gel was positioned at the ingress end of the bed. A feedstock containing 1.0 weight percent methanol and 300–700 ppm(w) dimethyl ether was passed through each of Bed A and Bed B at the same flow rate of 100 pounds per hours and temperature conditions. It was found that although the capacity of the two beds for dimethyl ether and methanol were essentially the same, the mass transfer zone in Bed A was 6 pounds of adsorbent whereas in the case of Bed B the mass transistion zone was only 3.9 pounds of adsorbent, representing a significant improvement over Bed A.

What is claimed is:

1. Process for preparing methyl tert.-alkyl ether which comprises the steps of:
    (a) contacting and reacting in the liquid phase a reaction mixture formed by combining a stream consisting essentially of hydrocarbons having from 4 to 5 carbon atoms and containing at least some proportion of an isoalkylene having from 4 to 5 carbon atoms with less than a stoichiometric excess of methanol, with respect to the isoalkylene, to form a reaction product comprising methyl tert.-alkyl ether, at least 50 ppm (w) unreacted methanol, unreacted $C_4$–$C_5$ hydrocarbons and at least 5 ppm (w) dimethyl ether;
    (b) isolating at least 99 percent (v) of the methyl tert.-alkyl ether from the reaction product;
    (c) recovering the unreacted methanol and dimethyl ether from the residual portion of the reaction product by passing said residual portion in the liquid phase and at a temperature of less than 60° C. through a first adsorption zone containing silica gel as the adsorbent whereby the methanol is selectively adsorbed thereon and thereafter passing the effluent from said first adsorption zone through a second adsorption zone containing zeolite 13X as the adsorbent whereby dimethyl ether is selectively adsorbed and non-adsorbed $C_4$–$C_5$ hydrocarbons are removed therefrom as the effluent and recovered;
    (d) regenerating the two adsorption zones by passing therethrough a non-sorbable purge fluid stream in such a manner that the purge fluid stream passes first through the said second adsorption zone and thereafter the effluent therefrom passes through the first adsorption zone whereby the second adsorption zone is not contacted with methanol desorbed from the first adsorption zone; and
    (e) recovering additional methanol and dimethyl ether respectively in the said first and second adsorption zones by passing an additional residual portion of the reaction product as defined in step (c) through the regenerated adsorption zones.

2. Process according to claim 1 wherein the first adsorption zone containing silica gel and the second adsorption zone containing zeolite 13X are contained within a single compound adsorption bed.

3. Process according to claim 1 wherein the isoalkylene reacted with methanol to form a methyl tert.-alkyl ether is isobutylene.

4. Process according to claim 3 wherein the dimethyl ether content of the reaction product of step (a) is from 5 to 3,000 ppm (w)

* * * * *